United States Patent [19]
Reider et al.

[11] Patent Number: 5,998,612
[45] Date of Patent: Dec. 7, 1999

[54] ANTIBIOTIC SYNTHESIS

[76] Inventors: Paul J. Reider, 621 Kimball Ave.; Edward J. J. Grabowski, 741 Marcellus Dr., both of Westfield, N.J. 07090

[21] Appl. No.: 07/898,348

[22] Filed: Jun. 12, 1992

Related U.S. Application Data

[63] Continuation of application No. 07/825,797, Jan. 21, 1992, abandoned, which is a continuation of application No. 07/744,664, Aug. 9, 1991, abandoned, which is a continuation of application No. 07/559,807, Jul. 30, 1990, abandoned, which is a division of application No. 07/463,020, Jan. 10, 1990, abandoned, which is a continuation of application No. 07/355,858, May 18, 1989, abandoned, which is a continuation of application No. 07/355,858, May 18, 1989, abandoned, which is a continuation of application No. 07/245,996, Sep. 14, 1988, abandoned, which is a continuation of application No. 07/212,107, Jun. 21, 1988, abandoned, which is a division of application No. 07/124,135, Nov. 23, 1987, abandoned, which is a division of application No. 07/065,189, Jun. 22, 1987, abandoned, which is a continuation of application No. 07/008,049, Jan. 15, 1987, abandoned, which is a continuation of application No. 06/872,715, Jun. 10, 1986, abandoned, which is a continuation of application No. 06/388,373, Jun. 14, 1982, abandoned, which is a continuation-in-part of application No. 06/367,532, Apr. 12, 1982, abandoned, which is a continuation-in-part of application No. 06/314,152, Oct. 23, 1981, abandoned.

[51] Int. Cl.[6] .......................... C07D 7/18; C07D 205/08; C07D 503/04; C07D 499/06
[52] U.S. Cl. ........................ 540/302; 540/200; 540/360; 540/347; 540/350
[58] Field of Search ................................... 540/200, 302, 540/350

[56] References Cited

U.S. PATENT DOCUMENTS 4,287,123 9/1981 Liu ............................................ 560/19
4,290,947 9/1981 Christensen ............................ 540/200

OTHER PUBLICATIONS

Karady, JACS 103, 6765(1981).
Oida, "Recent Advance in the Chemistry of Beta Lactam Antibiotics", p.330–348.
Reider, Tet. Letters 23, 379 (1982).
Chen, Tet. Letters 1977, p4183.
Paterson, Tet. Letters p 1519–1520 (1979).
Neetz I Chem Abs 95, 424465s,(1981).
Neetz II, Ang. Chem Int. Ed. 17, 48–9(1978).
Rasmussen, Synthesis 1977, p. 91.

*Primary Examiner*—Mark L. Berch
*Attorney, Agent, or Firm*—Sylvia A. Ayler; Richard C. Billups; Mark R. Daniel

[57] ABSTRACT

A method of preparing intermediates for carbapenem antibiotics characterized by treating a N-deprotected acetoxy conpound of the formula:

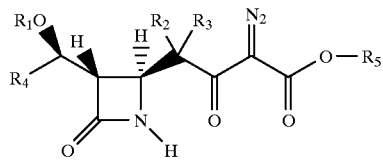

in the presence of a Lewis acid or a silylating agent to yeild an intermediate; and cyclizing the intermediate in the presence of rhodium (II) acetate to form a bicyclic ketoester.

4 Claims, No Drawings

ANTIBIOTIC SYNTHESIS

RELATED APPLICATION

This is a continuation, of application Ser. No. 07/825,797, filed Jan. 21, 1992 abandoned, which is a continuation, of application Ser. No. 07/744,664, filed Aug. 9, 1991, abandoned, which is a continuation, of application Ser. No. 559,807, filed Jul. 30, 1990, now abandoned, which is a division of Ser. No. 463,020, filed Jan. 10, 1990, now abandoned, which is a continuation of Ser. No. 355,858, filed May 18, 1989, now abandoned, which is a continuation of Ser. No. 245,996, filed Sep. 14, 1988, now abandoned, which is a continuation of Ser. No. 212,107, filed Jun. 21, 1988, now abandoned, which is a division of Ser. No. 124,135, filed Nov. 23, 1987, now abandoned, which is a division of Ser. No. 065,189, filed Jun. 22, 1987, now abandoned, which is a continuation of Ser. No. 008,049, filed Jan. 15, 1987, now abandoned, which is a continuation of Ser. No. 872,715, filed Jun. 10, 1986, now abandoned, which is a continuation of Ser. No. 388,373. filed Jun. 14, 1982, now abandoned, which is a cont-in-part of Ser. No. 367,532 filed Apr. 12, 1982, now abandoned, which is a continuation-in-part of Ser. No. 314,152 filed Oct. 23, 1981, now abandoned.

BACKGROUND OF THE INVENTION

The discovery of thienamycin of formula I and analogous 1-carbapenem antibiotics derived from various strains of Streptomyces has resulted in an intense interest in the synthesis of the novel carbapenem skeleton.

Although a chiral synthesis of thienamycin starting from L-aspartic acid has been achieved by Salzmann et al. and is described in U.S. Pat. No. 4,290,947, this earlier work entailed a large number of steps and the use of strenuous reaction conditions which are not amenable to commercial production. Of particular concern was the chemistry used to elaborate a side chain at the 4-position of an azetidin-2-one compound.

The formation of a carbon-carbon bond at the 4-position of an azetidin-2-one compound opens up a wide variety of synthetic pathways to the carbapenems. The known methods, however, suffer from low yields, complex reaction conditions, and functional group limitations.

OBJECTS OF THE INVENTION

It is, accordingly, an object of the present invention to provide an improved method for the synthesis of carbapenems including thienamycins, penems and oxapen-2-em-3-carboxylic acids. Another object is to provide a simpler and more economical method for the production of these antibiotics. A further object is to provide novel intermediates for the synthesis of these antibiotics. These and other objects of the present invention will be apparent from the following description.

SUMMARY OF THE INVENTION

A β-lactam formic acid is converted to a dianion by treatment with a very strong base followed by acylation to introduce an acyl group in the 3-position followed by reduction to form the corresponding 3-(1'-aryl or 1'-alkyl 1'-hydroxymethyl)-2-azetidinone-4-carboxylic acid. Direct alkylation of the dianion with aldehydes will also give the same hydroxymethyl-2-azetidinone-4-carboxylic acids. The latter compounds are then subjected to an oxidative decarboxylation with lead tetracetate to substitute an acetoxy group for the carboxyl group. The resulting N-deprotected 4-acetoxy compound is then treated with a silyl enolether in the presence of a Lewis acid to form a compound which is cyclized in known manner with rhodium (II) acetate to give the 1-carbapenem structure in near quantitative yield, or the acetoxy group is replaced with a triphenylmethylthio group which is then elaborated in known manner to give a penem.

DETAILED DESCRIPTION

The present invention relates to carbapenems including thienamycin, penems and oxapen-2-em-3-carboxylic acids and, more particularly, to a novel method for the synthesis of these antibiotics involving novel intermediates.

According to the present invention, L-aspartic acid of Formula A is converted to N,O,O-tristrimethylsilylaspartate of Formula B by silylation in known fashion, e.g., by use of hexamethyldisilazane in the presence of an acidic catalyst, or by use of trimethylsilyl chloride in the presence of an amine. The compound of Formula B is then treated with strong base to form the azetidinone formic acid of Formula C. By a strong base is meant a base having a p$K_a$>20. Examples of suitable bases are compounds of the formula RMgX wherein R is an alkyl group and X is a halide such as, for example, t-butyl MgCl or $CH_3$MgI, trialkyl aluminum such as, for example, trimethyl aluminum, lithium dialkylamides such as, for example, lithium diisopropyl amide, or metal alkoxides such as for example, lithium methoxide, sodium isopropoxide, K-t-butoxide or magnesium t-butoxide or alkali metal hydrides such as, for example, potassium hydride. The compound of Formula C is then N-protected to yield the compound of Formula 2.

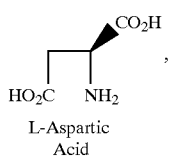

L-Aspartic Acid

A

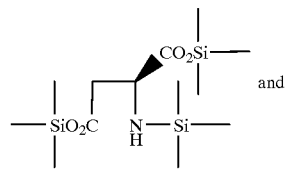
and

B

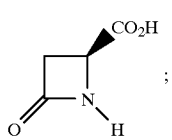

C

The N-protected lactam formic acid of Formula 2 is treated with a very strong base, that is, a base capable of converting the compound of Formula 2 into the dianion of Formula 3. The N-protecting group may be any readily removable nitrogen protecting group such as, for example, a tri-substituted silyl group wherein the substituents may be alkyl groups or aryl groups. Specific examples of suitable N-protecting agents are t-butyldimethylsilyl chloride, diphenylmethylsilyl chloride or dimethylisobutylsilyl chloride. Tosyl and benzyl are examples of other N-protecting groups. Examples of suitable strong bases are lithium diisopropyl amide, lithium hexamethyldisilamide, lithium 2,2,6,6-tetramethylpiperidide and butyl lithium. Lithium diisopropyl amide is a preferred base. The reaction takes place in the presence of an aprotic solvent such as, for example, tetrahydrofuran (THF), diethylether or dimethoxyethane. The resulting dilithium salt of Formula 3 is acylated with an acylating agent of the formula

wherein $R_4$ is alkyl of 1–4 carbons, or alkenyl of 2–4 carbons, phenyl, phenyl substituted by 1 to 3 alkyl groups of 1–3 carbon atoms, 1 to 3 halogen atoms, 1 to 3 trifluoromethyl groups, amino, cyano or nitro, and wherein X is a leaving group such as, for example, halide, acetoxy, alkoxy, imidazole, pyridylthio, arylthio or alkylthio. The acylation takes place in the presence of at least an additional equivalent of lithium diisopropyl amide to form a compound of Formula 4.

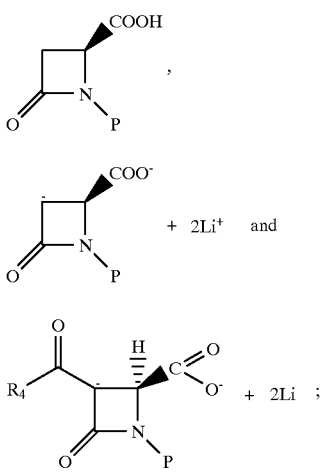

Alternatively, the N-protected lactam formic acid of Formula 2 may be reacted with at least 3 equivalents of base in which case the acylation reaction may take place without further addition of base.

The dilithium salt of Formula 3 may also be produced from the isolable mono-lithium salt of Formula 3a by treatment with one equivalent of lithium diisopropyl amide. The mono-lithium salt of Formula 3a is formed by reaction of an N-protected lactam formic acid of Formula 2 with one equivalent of a lithium base, for example, lithium hydride, lithium hydroxide, n-butyl lithium or lithium diisopropyl amide.

The dianion compound of Formula 4 may be reacted with 1 equivalent of acid to form the monoanion compound of Formula 5, or it may be reacted with 2 equivalents of acid to form the compound of Formula 6.

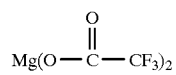

The dilithium salt of Formula 3 is alkylated with an aldehyde of the formula $R_4CHO$ to form an epimeric mixture of hydroxymethyl formic acid compounds of Formula 8a. This epimeric mixture may be oxidized with a variety of reagents such as, for example, sodium dichromate-sulfuric acid-water, chromium trioxide, or dimethyl sulfoxide-oxalyl chloride to the β-lactam keto acid compound of Formula 6.

Reduction of the ketoacid compounds of Formula 6 with standard reducing agents such as, for example, $NaBH_4$, $LiBH_4$, amine boranes, or $H_2$/catalysts, affords mixtures of epimers containing the R,S,S-substituted hydroxymethyl-β-lactam formic acid compounds of Formula 8. However, treatment of the compounds of Formula 5 and Formula 6 with $$Mg(O-\overset{O}{\underset{\|}{C}}-CF_3)_2$$

(magnesium trifluoroacetate) and diisopropyl amine borane stereospecifically yields the compounds of Formula 7 and Formula 8, respectively.

Furthermore, treatment of the compounds of Formula 7 with an acid also gives the compounds of Formula 8.

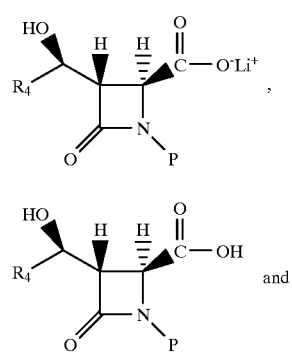

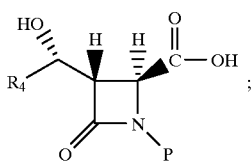

8a

The substituted hydroxymethylformic acid compound of Formula 8 or its N-deprotected analogue is reacted with lead tetraacetate to form the corresponding substituted hydroxymethyl acetoxy azetidinone of Formula 9 wherein $R_1$ is H or its N-deprotected analogue of Formula 10 wherein $R_1$ is H, respectively. The compound of Formula 9 wherein $R_1$ is H is then treated in known manner to remove the N-protecting group, for example, by use of trifluoro acetic acid, tetrabutyl ammonium fluoride, or methanol and aqueous hydrochloric acid, or acetone and aqueous hydrochloric acid to yield the deprotected substituted hydroxymethylacetoxy azetidinone compound of Formula 10 wherein $R_1$ is H.

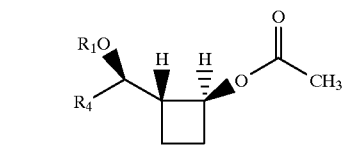

9

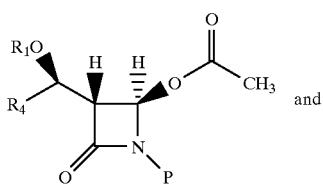

10

The epimeric substituted hydroxymethylformic acid compounds of Formula 8A are reacted with lead tetraacetate to form the corresponding substituted hydroxymethyl acetoxy azetidinones of Formula 9A wherein $R_1$ is H.

Alternatively, the compounds of Formula 8A may be converted directly to the compounds of Formula 10A wherein $R_1$ is H by carrying out the foregoing reaction at elevated temperatures of about 45° C. or above, preferably at from about 70° to about 75° C.

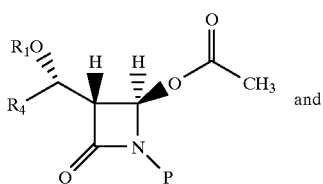

9A

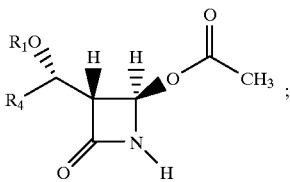

10A

This epimeric mixture of compounds of Formula 9A or its N-deprotected analogue of Formula 10A may be oxidized in known manner to the compound of Formula 19 where P is a protecting group, e.g. t-butyldimethylsilyl, or the compound of Formula 20 where P=H, respectively.

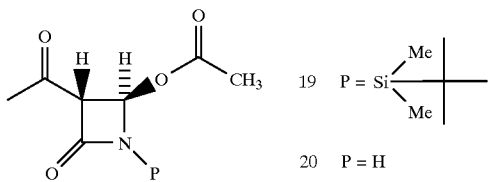

19  P = Si(Me)(Me)(t-Bu)

20  P = H

Reduction of the ketoacetate compounds of Formulas 19 or 20 with standard reducing agents such as, for example, $NaBH_4$, $LiBH_4$, amine boranes or $H_2$/catalysts, affords mixtures of epimers containing the R,R,R-substituted hydroxymethyl-β-lactam formic acid compounds of Formula 9 and 10. However, treatment of the compounds of Formula 19 and 20 with

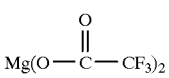

(magnesium trifluoroacetate) and diisopropyl amine borane stereospecifically yields the compound of Formula 9 and Formula 10, respectively.

Compounds of Formula 9 wherein $R_1$ is other than H are prepared by reacting the compound of Formula 9 (wherein $R_1$ is hydrogen) with a halide such as, for example, trimethylsilyl chloride, t-butyldimethylsilyl chloride or 4-nitrophenyl chloroformate.

PREPARATION OF CARBAPENEM COMPOUNDS

Treatment of the compound of Formula 10 with silyl enolether of Formula 11 wherein $R_2$ and $R_3$ are hydrogen or are independently alkyl of 1 to 4 carbon atoms, alkenyl of 2 to 4 carbon atoms, benzyl or phenethyl, in the presence of zinc halide or other Lewis acids such as, for example, boron trifluoride etherate, titanium tetrachloride, stannic chloride, aluminum chloride, and the like, or in the presence of a highly reactive silylating agent such as trimethylsilyl triflate, yields the esters of Formula 12 wherein $R_5$ may be, for example, benzyl, allyl, alkyl or p-nitrobenzyl. Monosubstituted compounds of Formula 11 when one of $R_2$ and $R_3$ is other than hydrogen are prepared following the procedure of Weiler, J.A.C.S. 1974, 96, 1082, by treating benzyl acetoacetate with sodium hydride followed by n-butyl lithium and then adding a halide containing the group to be introduced, e.g., methyl iodide, allyl bromide, or benzyl bromide. Diazotization and subsequent silyl enol ether formation gives the compounds of Formula 11. Disubstituted compounds of Formula 11 when $R_2$ and $R_3$ are both other than hydrogen are prepared in analogous fashion.

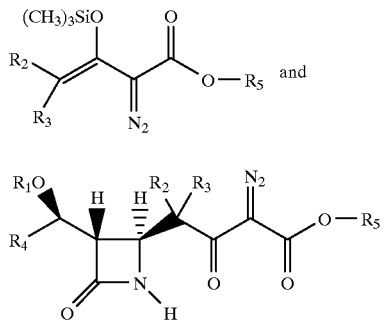

11

12

The compound of Formula 12 is then converted in known manner to a carbapenem, for example, as shown in Examples 15–18 of U.S. Pat. No. 4,290,947.

An alternate procedure for preparing the compounds of Formula 12 comprises reacting a compound of Formula 9 or 10 with a compound of Formula 13, wherein $R_2$ and $R_3$ have the same meaning as in the compound of Formula 11 and R is alkyl of 1–4 carbon atoms or a silyl group such as trimethyl silyl, in the presence of a Lewis acid or trimethylsilyl triflate or a trimethylsilylatedperfluorinated sulfonic acid resin to yield a compound of Formula 14.

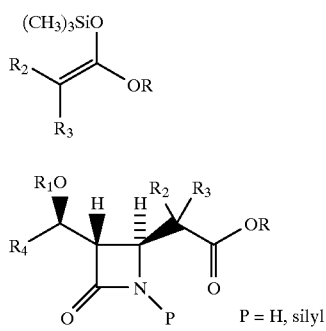

13

14

P = H, silyl

The latter compound is saponified to remove R if other than H (and $R_1$ is removed if other than H), the carboxyl group activated with carbonyl diimidazole and then reacted with $Mg(O_2CCH_2CO_2R_5)_2$, and finally subjected to diazo transfer to yield the compound of Formula 12.

PREPARATION OF OXAPEN-2-EM-3-CARBOXYLIC ACID COMPOUNDS

Treatment of the compound of Formula 10 with a 2-diazo malonate of Formula 15 wherein $R_6$ is an alkali metal or alkaline earth metal cation, e.g., Li, Na, K, Mg, or Cu, Ag, Zn or Cd, a trialkylsilyl radical, e.g., trimethyl silyl or t-butyldimethyl silyl, or a trialkyl ammonium salt, e.g., triethylammonium, and wherein $R_5$ has the same meaning as defined for the compound of Formula 11, gives the compound of Formula 16.

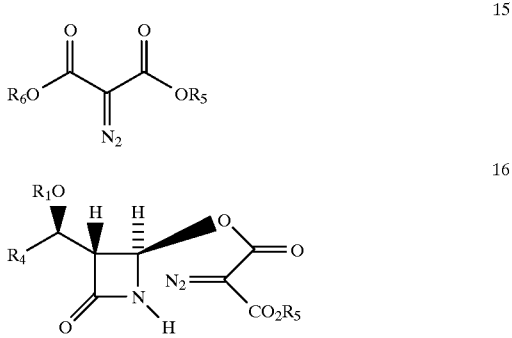

15

16

The compound of Formula 16 is converted to the compound of Formula 17 by a Rhodium (II) catalyzed cyclization and in turn through the compound of Formula V to the oxapen-2-em-3-carboxylic acid compound of Formula 18 (wherein $R_7$ is substituted or unsubstituted alkyl, aryl, heteroaryl, heterocyclyl or $SR_7$ wherein $R_7$ is as defined above). The compound of Formula 17 is treated with diphenylchlorophosphate in the presence of a tertiary amine to yield the compound of Formula V (see Example 7). In turn, the compound of Formula V is converted to the compound of Formula 18 by reaction with a metal alkyl, metal aryl, metal heteroaryl, metal heterocyclyl or $HSR_7$ wherein the metal is either Li, Na, K, Mg or Cd and $R_7$ is as defined above.

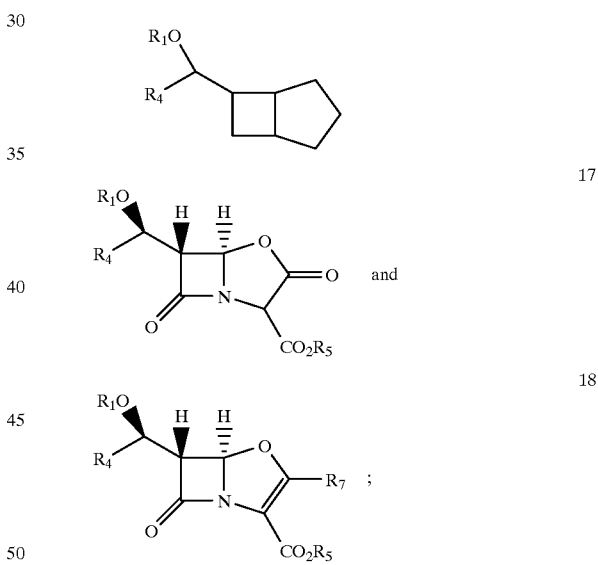

17 and

18

PREPARATION OF PENEM COMPOUNDS

Treatment of the compound of Formula 10 with sodium triphenylmethylthiolate yields the compound of Formula 21. The latter (when $R_1$ is other than H, for example, t-butyldimethylsilyl) may be converted sequentially by following the procedure of British patent 2,042,514 to the compounds of Formulas 22, 23, 24 and 25. The compound of Formula 22 is formed by treating the compound of Formula 21 successively with $OHCCO_2R_5$ (where $R_5$ has the same meaning as in the compound of Formula 11), $SOCl_2$, and triphenylphosphine. Treating the compound of Formula 22 with $AgNO_3$ yields the compound of Formula 23. Treating the latter with an acyl halide yields the compound of Formula 24, and heating the latter yields the compound of Formula 25.

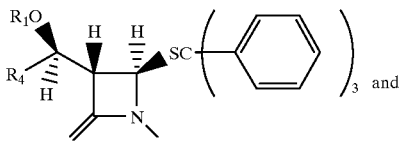

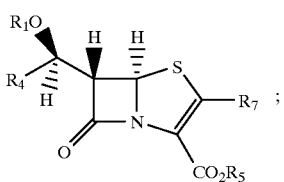

Alternatively, the compound of Formula 23 is reacted with chlorothionate,

to yield the compound of Formula 26 and the latter is converted by heat following the procedure of European patent application 13,662 and British patent 2,048,261 to the compound of Formula 27.

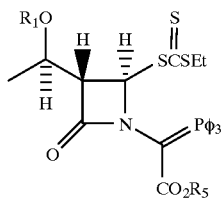

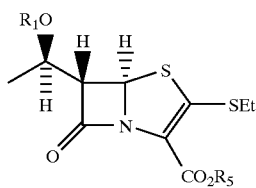

$R_1$=tBuMe$_2$Si, $R_5$=allyl $R_1$=PNBO$_2$C, $R_5$=PNB

The following examples illustrate the present invention without, however, limiting the same thereto. All temperatures are expressed in degrees Celsius.

EXAMPLE 1

Preparation of Thienamycin

A. Preparation of N-protected lactam formic acid of Formula 2.

To a 0° solution of the unprotected lactam, azetidinone-4-carboxylic acid benzyl ester (4.1 g, 20 mmol) prepared as described in U.S. Pat. No. 4,290,947, in 15 mL of sieve dried dimethylformamide (DMF) was added t-butyldimethylsilyl chloride (3.165 g, 21 mmol) followed by triethyl amine (2.93 mL, 21 mmol). After stirring at 0° for 40 minutes the reaction mixture was diluted with petroleum ether (200 mL) (low boiling) and washed with water. The organic layer was washed successively with 75 mL portions of water, 2N HCl, H$_2$O, brine and then dried over MgSO$_4$. Removal of the solvent gave N-t-butyldimethylsilyl azetidinone-4-carboxylic acid benzyl ester as a mobile oil in 93% yield (5.856 g).

B. Preparation of Deprotected lactam formic acid of Formula 2.

A solution of the protected lactam (4.452 g, 14.1 mmol) in absolute ethanol (20 mL) was treated with 10% Pd/C (400 mg) and hydrogenated at 40 psi at 25° for thirty minutes (until theoretical uptake of hydrogen had occurred). The catalyst was removed by filtration and the filtrate concentrated to yield the crystalline lactam formic acid of Formula 2 (mp 143–145°, [α]$_D$=–74°, c=1, CHCl$_3$) in 86% yield (2.775 g).

C. Dianion acylation and reduction.

The chiral acid of Formula 2 (458 mg, 2 mmol) in dry THF (2 mL) at 0° was added by a cannula to a 0° solution of 3.1 equivalents of lithium diisopropyl amide (6.2 mmol) in THF (6 mL) under nitrogen. The solution was then allowed to stir for 35 minutes during which time its temperature increased to 15°. The solution was then recooled to 0°. At this point the dianion solution was transferred via cannula to a 0° solution of acetylimidazole (330 mg, 3 mmol, 1.5 equivalents) in THF (4 mL) and stirred for thirty minutes during which time the temperature rose to room temperature. The resulting acetylated product was not isolated. After acidification to pH 7 with aqueous citric acid at 5° C., the mixture was treated with NaBH$_4$ (76 mg, 2 mmol) and stirred for one hour. After further acidification to pH 4 with citric acid, the resulting mixture was partitioned between ether and water followed by drying and evaporation of the ether layer to give an oil (470 mg, 86%). NMR spectra indicated that a mixture of the R,S,S and S,S,S isomers of Formula 8A (R$_4$=CH$_3$) was present in a 1.3 to 1 ratio, respectively.

D. Oxidative decarboxylation.

The hydroxyethyl formic acid of Formula 8 (R$_4$=CH$_3$) (400 mg, 1.46 mmol) in DMF (10 mL) and glacial acetic acid (2 mL) was treated with lead tetraacetate (714 mg, 1.61 mmol.) and warmed to 35° for 40 minutes. After cooling to room temperature, the DMF and acetic acid were removed under vacuum and the residue triturated with ether (100 mL). The ether layer was washed with aqueous perchloric acid, saturated NaHCO$_3$, brine, and dried over MgSO$_4$. Removal of the ether gave the hydroxyethylacetoxy azetidinone of Formula 9 (R$_4$=CH$_3$) in 84% yield (352 mg). The foregoing compound was then deprotected by treatment with trifluoroacetic acid to yield the deprotected compound of Formula 10 (R$_4$=CH$_3$). If desired, the protecting group may be removed prior to treatment with lead tetracetate.

E. Chain Extension.

A mixture of the hydroxyethylacetoxy azetidinone of Formula 10 (R$_4$=CH$_3$) (346 mg, 2 mmol) and silyl enol ether of Formula II (R=R$_3$=H, R$_5$=benzyl) (581 mg, 2 mmol), was dissolved in sieve dried dichloromethane (2 mL) and added to a suspension of fused (under vacuum) zinc iodide (639 mg, 2 mmol) in dichloromethane (6 mL). After stirring for 16 hours at 25° the mixture was poured into saturated NaHCO$_3$ (50 mL) and extracted with ethylacetate (200 mL). The ethylacetate layer was washed with brine, dried over MgSO$_4$, and concentrated to an oil. Chromatography on silica gel gave the compound of Formula 12 (R$_2$=R$_3$=H, R$_4$=CH$_3$, R$_5$=benzyl) in 89% yield (590 mg).

F. Preparation of (5R, 6S) Benzyl 6-[(R)-1-hydroxyethyl]-1-azabicyclo[3.2.0]heptan-3,7-dione-2-carboxylate.

A suspension of (3S,4R)-3-[(R)-1-hydroxyethyl]-4-[3-benzyloxycarbonyl-2-oxo-3-diazopropyl] azetidin-2-one (50 mg, 0.15 mmol) and rhodium (II) acetate (0.1 mg) in dry benzene (3 mL) was deoxygenated by bubbling through nitrogen for 10 minutes. The mixture was then heated to 78° for 1 hour. During heating the solid starting material gradually went into solution. The mixture was then cooled, filtered to remove the catalyst, and the filtrate was concentrated in vacuo to yield (5R, 6S) benzyl 6-[(R)-1-hydroxyethyl]-1-azabicyclo[3.2.0]heptan-3,7-dione-2-carboxylate, 45 mg. (98%) as a colorless oil.

G. Preparation of p-Nitrobenzyloxycarbonylaminoethanethiol.

To 600 mL diethyl ether ($Et_2O$)—75 mL $H_2O$ in an ice bath with stirring was added 3.2 g cysteamine hydrochloride (mw=114; 28.1 mmole). A solution of 7.14 g $NaHCO_3$ (mw=84; 85 mmole) in 75 mL $H_2O$ was added. The ice bath was removed, and at room temperature a solution of 6.75 g p-nitrobenzyl-chloro-formate (mw=216; 31.3 mmole) in 270 mL $Et_2O$ was added dropwise over a period of one hour. After 10 additional minutes, the layers were separated. The ether layer was extracted with 150 mL 0.25 N HCl, and then with 200 mL brine. Each aqueous layer was then backwashed successively with 100 mL $Et_2O$. The combined $Et_2O$ layers were dried over anhydrous $MgSO_4$ filtered, and concentrated under a $N_2$ stream. The crystalline residue was slurried in a small amount of ether, filtered, and the pale yellow crystals were dried under high vacuum to give 4.7 g. p-nitrobenzyloxycarbonylaminoethanethiol (65% yield).

H. Preparation of (5R,6S) Benzyl 3[2-(p-nitrobenzyloxycarbonyl)amino ethylthio]-6-[(R)-1-hydroxyethyl)-1-azabicyclo [3,2,0]-hept-2-en-7-one-2-carboxylate.

(5R,5S) Benzyl 6-[(R)1-hydroxyethyl]-1-azabicylco [3,2,0]heptan-3,7-dione-2-carboxylate (45 mg, 0.147 mmol) was dissolved in acetonitrile (3 mL) and the resulting solution was cooled to 0°. Diisopropylethylamine (22 mg, 0.17 mmol) was added by syringe and the resulting solution was stirred at 0° for 1 minute prior to the addition of a solution of freshly recrystallized p-toluene sulfonic anhydride (51 mg, 0.156 mmol) in dry acetonitrile (1 mL). The resulting solution was stirred at 0° for 1 hour to provide (5R, 6S) benzyl 3-(p-toluenesulfonyloxy)-6-[(R)-1-hydroxyethyl]-1-azabicyclo[3.2.0]-hept-2-en-7-one-2-carboxylate, then cooled to −25°. Diisopropylethylamine (80.5 mg, 0.624 mmol) was added by syringe followed shortly thereafter by a solution of N-p-nitrobenzyloxycarbonyl-aminoethanethiol (40 mg, 0.156 mmol) in 1 mL of dry acetonitrile. The reaction mixture was then stored in a refrigerator for 16 hours. The mixture was diluted with 25 mL of ethyl acetate washed with brine and dried over magnesium sulfate. Solvents were removed in vacuo to yield a yellow oil which was chromatographed on a silica gel plate (ethyl acetate) to yield (5R, 6S) benzyl-3-[2-(p-nitro-benzyloxycarbonyl)amino ethylthio]-6-[(R)-1-hydroxyethyl]-1-azabicyclo [3,2,0]-hept-2-en-7-dione-2-carboxylate as a yellow oil.

I. Preparation of Thienamycin.

A mixture of N-p-nitrobenzyloxycarbonyl thienamycin benzyl ester (9.5 mg, 0.017 mmol) and 10% Pd/C-Bolhofer type in tetrahydrofuran (2 mL), 0.1 M dipotassium hydrogen phosphate solution (1.4 mL) and 2-propanol (0.2 mL) was hydrogenated at 40 psi on the Parr shaker for 30 minutes. The mixture was then filtered and the catalyst was washed with water (3×3 mL.) The combined filtrate and washings were extracted with ethyl acetate-ethyl ether then concentrated to ~3 mL and lyophilized. The resulting white powder is identical to natural thienamycin in all respects.

EXAMPLE 2

Dianion Alkylation, Oxidation, and Stereospecific Reduction

A. Dianion Alkylation.

The chiral acid of Formula 2 (690 mg, 3 mmol) in dry THF (6 mL) at 0° was added to a 0° solution of 2.07 equivalents of lithium diisopropyl amide (6.2 mmol) in THF (2 mL) under nitrogen. The solution was then allowed to stir for 35 minutes during which time its temperature increased to 25°. The solution was then recooled to 0°. At this point the 0° dianion solution was treated with excess acetaldehyde (0.5 mL) and stirred for 10 minutes during which time the temperature rose to 25°. After recooling to 0° the mixture was acidified with aqueous citric acid and then partitioned between ether and water. Drying and evaporation of the ethereal layer gave the hydroxyethylformic acid compound of Formula 8A ($R_4=CH_3$) as an oily mixture of hydroxyl epimers (734 mg, 90%).

B. Oxidation.

The epimeric hydroxyethylformic acid compounds of Formula 8A ($R_4=CH_3$) (676 mg) (2.47 mmol) were dissolved in ether (15 mL), diluted with petroleum ether (5 mL) and cooled to −20°. To this solution was added dropwise 5 mL of a 2 Molar $Na_2Cr_2O_7$ solution (100 g, $Na_2Cr_2O_7$, 300 mL $H_2O$ 136 g $H_2SO_4$, mixture diluted to 500 mL total volume with $H_2O$). After stirring at −20° C. for 1.5 hours the mixture was partitioned between ether and ice water. The ethereal layer was dried and evaporated to yield the acetylformic acid compound of Formula 6 ($R_4=CH_3$) as an oil (430 mg, 64%).

C. Stereospecific Reduction.

A solution of the acetylformic acid compound of Formula 6 ($R_4=CH_3$) (88 mg, 0.32 mmol) in ether (5 mL) was cooled to −78° and treated first with magnesium trifluoroacetate (425 mg) and then with diisopropylamine borane (80 mg) in ether (1 mL). The mixture was stirred for 1 hour during which time its temperature rose to 25°. After acidification with aqueous citric acid the resulting mixture was partitioned between dichloromethane and water followed by drying and evaporation to give an oil in 85% yield. The NMR spectra indicated that only the R,S,S isomer of Formula 8 ($R_4=CH_3$) was present.

D. The R,S,S isomer of Formula 8 is then treated as described in steps D through H of Example 1 to yield thienamycin.

EXAMPLE 3

Alternate Synthesis of Triethylamine Salt of Azetidinone Formic Acid of Formula C A. Preparation of N,O,O-Tristrimethylsilylaspartate.

L-Aspartic acid (13.31 g, 100 mmol) was suspended in hexamethyldisilazane (60 mL) and treated with concentrated $H_2SO_4$ (4 drops). After refluxing (125° C.) for 16 hours the excess hexamethyldisilazane was removed in vacuo to yield the trisilyl aspartate, N,O,O-trismethylsilylaspartate, (32.9 g, 94%). The liquid product could be distilled—b.p. 84–93° C. α 0.05 mm.

B. Preparation of Triethylamine Salt of Azetidinone Formic Acid of Formula C.

The trisilylaspartate (4.786 g, 13.688 mmol) in ether (80 mL) was cooled to 0° C. and then added via cannula to a solution of t-butyl-magnesium chloride (9 mL of 2.3 M in $Et_2O$; 20.7 mmol) in ether (10 mL) at 0° C. The mixture was warmed to 25° C. and allowed to stir 4 hours. After recooling to 0° C. approximately 40 mL of Dowex 50 resin (acidic) were added and the mixture was extracted with water. The aqueous layers were washed with $CCl_4$ and assayed by HPLC. Yield—700 mg, 44%. Isolation was achieved by treatment with $Et_3N$ and removal of water to give the stable triethylamine salt of azetidinone formic acid of Formula C.

EXAMPLE 4

Synthesis of N(t-butyldimethylsilyl)Azetidinone Formic Acid of Formula 2

A solution of the triethylamine salt of azetidinone formic acid of Formula C (650 mg, 5.6 mmol) in DMF (8 mL) was cooled to 0° C. and treated with triethylamine (5.6 mmol) and t-butyldimethylsilyl chloride (11.76 mmol). After stirring at 0° C. for 1 hour the DMF was removed under vacuum and the residue was dissolved in ether. The ether layer was washed with 1N HCl, $H_2O$, brine, dried over $MgSO_4$, filtered and concentrated to yield crystalline N-silyl acid of Formula 2 (1.259 g, 98%). $[\alpha]_D^{25}=-74°$ (c=1, $CHCl_3$), m.p. 143–145° C.

EXAMPLE 5

Synthesis of Epimeric Mixture of Deprotected Hydroxy Acetates of Formula 10A and Conversion to Hydroxy Acetates of Formulas 9 and 10

A. Preparation of Epimeric Mixture of N-Protected Hydroxy Acetates of Formula 9A.

The epimeric mixture of hydroxyethyl formic acids of Formula 8A ($R_4=CH_3$) (7.47 g, 27.3 mmol) in DMF (137 mL) and glacial acetic acid (27 mL) was treated with lead tetraacetate (18.17 g, 41 mmol) and warmed to 32° C. for 1.5 hours. After cooling to room temperature, the D14F and acetic acid were removed under vacuum and the residue was triturated with ether (150 mL). After filtering the insoluble lead salts, the ether filtrate was washed with brine (125 mL), dried ($MgSO_4$), and concentrated to an oil. The oil was dissolved in petroleum ether, washed with brine, dried, and concentrated to give, the epimeric mixture of hydroxy acetates of Formula 9A ($R_4=CH_3$) (5.51 g, 70%).

B. Preparation of Epimeric Mixture of Deprotected Hydroxy Acetates of Formula 10A.

One equivalent of the epimeric mixture of hydroxy acetates of Formula 9A ($R_4=CH_3$) was treated at 0° C. with 1 equivalent of t-butylammonium fluoride in tetrahydrofuran (THF) and 2 equivalents of acetic acid. Removal of the THF followed by silica gel chromatography gave the solid epimeric mixture of hydroxy acetates of formula 10A ($R_4=CH_3$).

C. Direct Preparation of Deprotected Hydroxy Acetates of Formula 10A from Protected Hydroxy Acetates of Formula 8A.

Carrying out the reaction of Step A at 70–75° C. effected concurrent desilylation of the lactam nitrogen to give the epimeric mixture of hydroxy acetates of Formula 10A.

D. Preparation of Enantiomerically Pure Protected Keto-Acetate of Formula 19.

A solution of the epimeric hydroxyethyl acetoxy azetidinones of Formula 9A in dichloromethane (11.7 g, 40.7 mmol, in 50 mL $CH_2Cl_2$) was added to a suspension of pyridinium chlorochromate (17.55 g, 81.4 mmol) and anhydrous sodium acetate (1.67 g, 20.35 mmol) in $CH_2Cl_2$ (100 mL) at room temperature. After 12 hours the mixture was diluted with 400 mL of ether and filtered through Florasil. After removal of the solvents in vacuo 10.1 q of a single, enantiomerically pure keto-acetate of Formula 19 was isolated (86%).

E. Prenaration of Enantiomerically Pure Deprotected Keto-Acetate of Formula 20.

A solution of the epimeric hydroxyethyl azetidinones of Formula 10A in dichloromethane (20 mmol in 20 mL $CH_2Cl_2$) was added to a suspension of pyridinium chlorochromate (8.77 q, 40 mmol) and anhydrous sodium acetate (0.84 g, 10 mmol) in $CH_2Cl_2$ (50 ml) at room temperature. After 8 hours the mixture was diluted with 200 ml of ether and filtered through a pad of Florasil. After removal of the solvents in vacuo the keto acetate of Formula 20 was isolated in 74% yield.

F. Preparation of Hydroxyacetate of Formula 10.

A solution of the chiral keto acetate of Formula 19 (10.0 g, 35 mmol) in anhydrous ether (300 mL) was cooled to −78° C. and treated with ethereal magnesium trifluoroacetate (86 mL of 2M solution). After stirring 5 minutes the mixture was treated with a solution of diisopropylamine borane (6.0 g) in ether (95 mL). The −78° C. cooling bath was replaced with an ice-water bath after 10 minutes and the mixture was stirred for 40 minutes. At this time cold 1N HCl (200 mL) was added and the mixture extracted. The aqueous layer was washed with ether (2×100 mL) and the combined organic layers were neutralized with aqueous $NaHCO_3$. After washing with brine (200 mL) the ether layer was dried ($MgSO_4$) and concentrated to an oil (9.55 g).

The oily hydroxyacetate 9 from above was dissolved in THF (40 mL), cooled to 0° C. and treated with glacial acetic acid (3.5 mL) followed by tetrabutylammonium fluoride (33 mL of 1M solution in THF). After 1 hour at 0° C. the mixture was concentrated to an oily mass and purified on silica gel to yield 4.2 g (69% from starting compound of Formula 19) of crystalline hydroxyacetate of Formula 10 (MP 109–113° C.), ($[\alpha]_D=+86°$, c=0.5, $CHCl_3$).

EXAMPLE 6

Synthesis of Chain Extended Hydroxyethyl Acetoxy Azetidinone of Formula 12

A. Preparation of Benzyl 3-Oxopentanoate

Following the procedure of Weiler, J. Am. Chem. Soc. 1974, 96, 1082, benzyl acetoacetate, 7.68 g (40 mmol) was added dropwise to a 0° C. suspension of sodium hydride (2.1 g of 50% dispersion, 42 mmol) in THF (100 mL). After stirring for 10 minutes n-butyl lithium (16 mL of 2.5 M in hexane) was added and the mixture was aged for an additional 10 minutes. At this time iodomethane (2.74 mL, 44 mmol) in THF (4 mL) was added dropwise and the mixture aged 1 hour while slowly warming to room temperature. Work-up was achieved by quenching at 0° C. with 1N HCl, extracting with ether, washing the ether with aqueous $NaHCO_3$, brine, and drying with $MgSO_4$. Removal of the solvent yielded benzyl 3-oxopentanoate.

B. Preparation of Benzyl 2-Diazo-3-Oxopentanoate.

Following the procedure described in U.S. Pat. No. 4,284,575 a 0° C. mixture of benzyl 3-oxopentanoate (1.05 g, 5.1 mmol) napthalene-2-sulfonylazide (1.306 g, 5.6 mmol), and triethylamine (0.76 mL, 5.4 mmol) in acetonitrile (6 mL) was aged overnight (0°–25° C.). After dilution with ether, washing with aqueous $H_3PO_4$, aqueous $NaHCO_3$, brine, drying ($MgSO_4$), and concentration, the oily product was chromatographed on silica gel (4:1 hexane:EtOAc) to give 975 mg (82%) of the benzyl 2-diazo-3-oxopentanoate. NMR ($CCl_4$) δ: 1.2, 3H (t, J=7.5 Hz); 2.9, 2H (q, J=7.5 Hz); 5.3, 2H (S); 7.3, 5H (S).

C. Preparation of Silyl Enol Ether of Benzyl 2-Diazo-3-Oxopentanoate.

A solution of benzyl 2-diazo-3-oxopentanoate (330 mg, 1.42 mmol) in THF (1.2 ml) was added to a −78° C. solution of tetramethylethylenediamine (TMEDA-0.28 mL), hexamethyldisilazane (0.37 mL), and n-butyl lithium (0.71 ml of 2.5 M) in THF (12 mL). After 10 minutes chlorotrimethyl silane (0.23 mL) was added and the mixture warmed slowly to 25° C. After 1 hour at 25° C. the mixture was concentrated in vacuo and the residue triturated with hexane. The hexane insoluble material was removed by filtration and the filtrate was concentrated to yield 394 mg (91%) of the oily silyl enol ether. NMR ($CDCl_3$) δ: 1.6, 3H (d, J=7 Hz), 5.1, 2H (S); 5.1, 1H (q, J=7 Hz), 7.2, 5H (S).

D. Preparation of Chain Extended Hydroxy-Ethyl Acetoxy Azetidinone of Formula 12

A mixture of the hydroxyethyl acetoxy azetidinone of Formula 10 (112 mg, 0.65 mmol) and silyl enol ether of benzyl 2-diazo-3-oxopentanoate (394 mg, 1.3 mmol) was dissolved in sieve dried dichloromethane (2 mL) and added to a suspension of fused (under vacuum) zinc chloride (55 mg, 0.4 mmol) in dichloromethane (2 mL). After refluxing gently for 12 hours, the mixture was poured into saturated NaHCO$_3$ (50 mL) and extracted with ethyl acetate (100 mL). The ethyl acetate layer was washed with brine, dried over MgSO$_4$, and concentrated to an oil. Chromatography on silica gel gave the compound of Formula 12 in 77% yield.

EXAMPLE 7

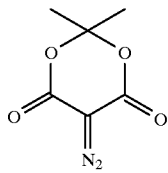

I

To a solution of 5-diazo-4,6-diketo-2,2-dimethyl-1,3-dioxane (diazo Meldrum's acid) of Formula I (170.13 g, 1 mole) in THF (250 ml) is added p-nitrobenzyl alcohol (153.14 g, 1.0 mole). The mixture is stirred at 25° C. for 8 hours, diluted with ether (500 mL), the crystalline product removed by filtration, and vacuum dried to yield 223 g (84%) of the diazo half acid-ester of Formula 15 wherein R$_6$ is H and R$_5$ is p-nitrobenzyl.

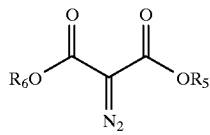

15

A solution of the diazo half acid ester of Formula II (2.652 g, 10 mmol) in dichloromethane (10 mL) is cooled to 0° C., treated with triethylamine (1.4 mL, 10 mmol), and then the R,R,R-4-acetoxy-3-(1-hydroxyethyl)-2-azetidinone of formula 10 is added. After stirring at 25° C. for 4 hours, the reaction mixture is diluted with CH$_2$Cl$_2$ (50 mL), washed with brine (25 mL), and dried (Na$_2$SO$_4$). After concentration the residual oil is chromatographed on silica gel to yield the diazo malonate of formula 16 (2.16 g, 57%) as a pale yellow solid, wherein R$_1$ is H, R$_4$ is methyl and R$_5$ is p-nitrobenzyl.

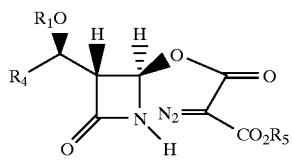

16

The diazo malonate of Formula 16 (378 mg, 1 mmol) is suspended in dichloromethane (4 ml) and treated with a catalytic amount of Rhodium (II) acetate dimer (5 mg). The slurry is stirred at 40° C. until it becomes homogeneous. The resulting solution is cooled to 25° C. and treated with hexanes to precipitate the product. Filtration and washing with hexanes gives the compound of Formula 17 (343 mg, 98%), wherein R$_1$ is H, R$_4$ is methyl and R$_5$ is p-nitrobenzyl.

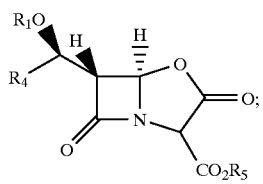

17

A solution of the oxapenem compound of Formula 17 (343 mg, 0.98 mmol) in dichloromethane is treated with diisopropylethylamine (0.174 ml, 1.0 mmol) and diphenylchlorophosphate (268 mg, 0.99 mmol). The resulting solution of V is used without modification.

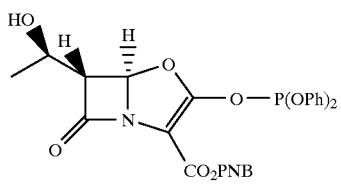

V and

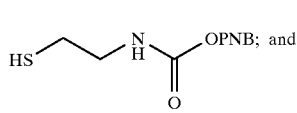

VI

The above solution of compound V is treated with diisopropylethyl amine (0.174 ml, 1.0 mmol) and the N-protected cysteamine VI (256 mg, 1.0 mmol). The mixture is stirred at 25° C. for 14 hours until all of the product precipitates. The crystalline bis-protected oxapenem of Formula 28 is isolated by filtration and washed with CH$_2$Cl$_2$:hexane (1:1) to give 492 mg (0.81 mmol, 83%).

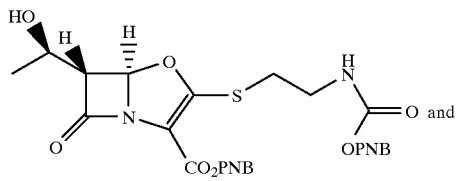

28

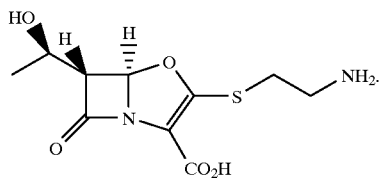

18a

The bis-protected oxapenem of Formula 28 (492 mg, 0.81 mmol) is mixed with 10% Pd/C, THF (100 mL), 0.1 M dipotassium hydrogen phosphate solution (70 mL) and 2-propanol (10 mL). This mixture is hydrogenated at 40 psi on a Parr Shaker for 40 minutes. The mixture is then filtered and the catalyst is washed with water (2×100 mL). The combined filtrate and washings are extracted with ethylacetate-ethyl ether then the aqueous layer is concentrated to 100 mL and lyophilized to yield the oxapenem of Formula 18a as a white solid.

EXAMPLE 8

Synthesis of Methyl Compound of Formula 14 from N-Deprotected Compound of Formula 10

A solution of the O-t-butyldimethylsilyl azetidinone compound of Formula 10 wherein $R_1$ is t-butyldimethylsilyl and $R^4$ is methyl (14.4 mg, 0.05 mmol) in anhydrous $CH_2Cl_2$ (0.05 ml) was cooled in a dry ice $Me_2CO$ bath under a $N_2$ atmosphere. Silylenol ether of Formula 13 wherein R and $R_3$ are methyl and $R_2$ is H (25 µl, 0.15 mmol) and $Me_3SiOTf$ (10 µl, 0.055 mmol) were added and the solution allowed to gradually warm to room temperature. After 3 hours, TLC showed some starting material. After 6 hours, the solution was diluted with EtOAc, washed with 5% $NaHCO_3$ and brine, dried with $MgSO_4$, filtered, and evaporated in vacuo to a white solid (13.5 mg, 86%). NMR showed a clear 1:1 mixture of α- and β-methyl products of Formula 14 wherein $R_1$ is t-butyldimethylsilyl, $R_4$ is methyl, $R_2$ is H, and R and $R_3$ are each methyl. No starting material or N-silyl products were apparent.

EXAMPLE 9

Synthesis of Methyl Compound of Formula 14 from N-Protected Compound of Formula 10

$ZnI_2$ (13.8 mg, 0.043 mmol) was fused under a $N_2$ atmosphere. After cooling to room temperature the $ZnI_2$ was treated with a solution of the N-trimethylsilyl protected compound of Formula 9 wherein $R_1$ is t-butyl-dimethylsilyl, $R^4$ is methyl, and P=trimethylsilyl (31 mg, 0.086 mmol) in anhydrous $CH_2Cl_2$ (430 µl) and with silyl enol ether of Formula 13 wherein R and $R_3$ are methyl and $R_2$ is H (40 µl, 0.25 mmol). The resulting mixture was stirred vigorously at room temperature for 2 hours, then diluted with EtOAc, washed with 5% $NaHCO_3$ and brine, dried with $MgSO_4$, and evaporated in vacuo to a clear oil (31.2 mg).

The crude product was dissolved in anhydrous THF (130 µl) and cooled in an ice-bath under a $N_2$ atmosphere. HOAc (9.8 µl, 0.17 mmol) and 1M $Bu_4NF$ (86 µl) were added and the solution was kept at 0° for 1 hour. The solution was diluted with EtOAc, washed with $H_2O$, 5% $NaHCO_3$ and brine, dried with $MgSO_4$, filtered, evaporated in vacuo and stripped with toluene to provide an off-white semi-solid (24 mg). Analysis of the NMR spectrum revealed a 5:4 mixture of α- and β-methyl products having the same composition as for example 8.

EXAMPLE 10

Synthesis of Methyl Compound of Formula 14 from N-Deprotected Compound of Formula 10

$ZnI_2$ (8.0 mg, 0.025 mmol, freshly fused under a $N_2$ stream) was suspended in anhydrous $CH_2Cl_2$ (250 µl) and treated with the acetoxy azetidinone of Formula 10 wherein $R_1$=t-butyl-dimethylsilyl and $R_4$ is methyl (14.4 mg, 0.05 mmol) and the silyl enol ether of Formula 13 wherein R and $R_3$ are methyl and $R_2$ is H (25 µl, ~0.15 mmol). The resulting mixture was vigorously stirred at room temperature for 70 minutes then diluted with EtOAc, washed with 5% $NaHCO_3$ and brine, dried with $MgSO_4$, filtered and evaporated in vacuo to a clear oil (19 mg). NMR analysis indicated a clean mixture of the N-trimethyl silylated starting material and the N-trimethylsilyl α- and β-methylmethoxy carbonyl products in a ratio of 20:63:17.

The crude product was dissolved in anhydrous THF (75 µl) and cooled in an ice-bath under a $N_2$ atmosphere. HOAc (5.7µ, 0.1 mmol) and 1M $Bu_4NF/THF$ (50 µl) were added and the solution was kept in an ice bath for 1 hour. The solution was diluted with EtOAc, washed with $H_2O$, 5% $NaHCO_3$ and brine, dried over $MgSO_{41}$ filtered, and evaporated in vacuo to a white solid (11 mg). NMR showed a mixture consisting of about 19% starting material, 63% α-Me product, and 18% β-Me product. The ratio of α to β products of Formula 14 wherein $R_1$ is t-butyldimethylsilyl, $R_2$ and $R_4$ are methyl, and $R_3$ is hydrogen, was about 3.5:1.

EXAMPLE 11

Synthesis of Compound of Formula 21

Trityl mercaptan (27.6, 0.1 mmol) and the azetidinone compound of Formula 10 wherein $R_1$ is H and $R_4$ is methyl (17.5 mg, 0.1 mmol) were added to an ice-cold, stirring solution of NaOMe (5.4 mg, 0.1 mmol) in anhydrous MeOH (1.0 mL). The cooling bath was removed and the solution was stirred 1 hour under a $N_2$ atmosphere. The solution was diluted with MeOH and evaporated in vacuo. The residue was taken up in EtOAc, washed with brine, dried over $MgSO_4$, filtered and evaporated in vacuo to give an oil (52 mg). The crude product was chromatographed on a 1 mm×20×20 cm SG GF plate using EtOAc as the developing solvent. The major UV visible band was removed and eluted with EtOAc to give the 4-$SCO_3$ azetidinone of formula 21 wherein $R_1$ is H and $R_4$ is $CH_3$ as an oil (77%) which slowly solidified on standing.

EXAMPLE 12

Synthesis of Compound of Formula 26

To a stirred suspension of 1.83 g of the compound of Formula 23 ($R_5$=p-nitrobenzyl, $R_1$=p-nitrobenzyloxycarbonyl) in 15 mL sieve dried $CH_2Cl_2$ at room temperature is added sequentially 347 mg of neat ethylchlorodithioformate and then 212 mg of pyridine. The mixture is stirred at room temperature under $N_2$ for 1.5 hours. The insolubles are filtered off, and the filtrate is washed well with EtOAc, and partitioned between EtOAc/ice-$H_2O$/2.5N aqueous HCl. The organic phase is separated, washed with saturated NaCl, saturated $NaHCO_3$, dried over $Na_2SO_4$, filtered and evaporated and dried in vacuo to a dark foam, over-night. The product is purified by chromatography on 50 g EM-60 silica gel, packed in toluene and eluted with toluene-EtOAc, 3:1 to give 1.5 g of desired product of Formula 26 ($R_5$=p-nitrobenzyl, $R_1$=p-nitrobenzyloxycarbonyl) as a yellow foam.

EXAMPLE 13

Synthesis of Compound of Formula 26

To a stirred solution of the compound of Formula 22 ($R_1$=t-butylmethylsilyl, $R_5$=p-nitrobenzyl) in 90 mL MeOH and 22.5 mL $CH_2Cl_2$ is added at room temperature 2.08 mL (2.04 g, 1.48 eq., $2.58×10^{-2}$ moles) of neat pyridine and then 139.4 mL of 0.15 M $AgNO_3$ in MeOH solution ($2.09×10^{-2}$ moles, 1.2 equivalents). The mixture is stirred at room temperature under $N_2$ for 0.5 hour and then concentrated to a dark solution. The concentrate is partitioned between $CH_2Cl_2$/ice-$H_2O$ and the organic phase was separated, dried over $Na_2SO_4$, filtered, and evaporated and dried in vacuo.

The above residue is dissolved in 125 ml of $CH2Cl_2$ and stirred at room temperature. To the stirred solution there is added 1.4 mL (1.38 g, $1.74×10^{-2}$ moles, 1 equivalent) of neat pyridine and then 2.25 mL (2.92 g, $2.09×10^2$ moles, 1.2 equivalents) of ethyldithiochloroformate. The mixture is stirred at room temperature under $N_2$ for 0.5 hour and then the insolubles are filtered off through Celite and washed well with $CH_2Cl_2$. The filtrate is evaporated and the residue partitioned between EtOAc/ice-$H_2O$/conc. HCl. The organic phase is separated, washed with saturated NaCl, ice-cold dilute aqueous NaHCO$_3$, and again with saturated NaCl. The product is dried over anhydrous Na$_2$SO$_4$, filtered, evaporated, and dried in vacuo overnight. The dark residue is purified by column chromatography on 500 mg EM-60 silica gel packed in CH$_2$Cl$_2$, and eluted initially with CH$_2$Cl$_2$, then with 2 liters CH$_2$Cl$_2$-EtOAc (20:1) and finally with 9 liters CH$_2$Cl$_2$-EtOAc (10:1) to give 8.97 g of yellow product wherein R$_1$ and R$_5$ correspond to the substituents in the starting material.

What is claimed is:

1. A process of synthesizing a carbapenem intermediate of the formula:

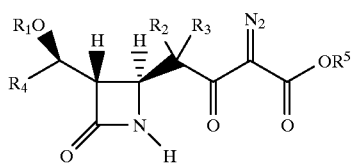

comprising:

treating a N-deprotected acetoxy compound of the formula:

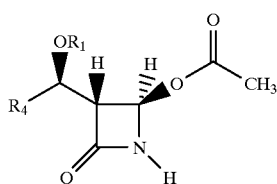

wherein R$_1$ is H, trialkylsilyl, triarylsilyl, diarylalkylsilyl or aryldialkylsilyl, wherein the alkyl portions of said groups contain 1–4 carbon atoms, and the aryl portions of said groups are selected from the group consisting of phenyl, p-nitrobenzylcarbonate or phenyl substituted with one to three groups selected from C$_1$ to C$_3$ alkyl, halo, trifluoromethyl, amino, cyano and nitro;

R$_4$ represents C$_{1-4}$ alkyl, C$_{2-4}$ alkenyl, phenyl, phenyl substituted by one to three groups selected from C$_1$ to C$_3$ alkyl, halo, trifluoromethyl, amino, cyano and nitro, with a silyl enolether of the formula:

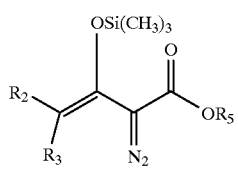

wherein:

R$_2$ and R$_3$ are independently H, C$_1$ to C$_4$ alkyl, C$_2$ to C$_4$ alkenyl, benzyl or phenethyl; and R$_5$ represents benzyl, allyl, C$_{1-4}$ alkyl, or p-nitrobenzyl, in the presence of a Lewis acid selected from the group consisting of zinc halide, boron trifluoride etherate, titanium tetrachloride, stannic chloride and aluminum chloride or a silylating agent having sufficient reactivity to yield said intermediate.

2. A process of synthesizing a carbapenem intermediate in accordance with claim 1, further comprising:

cyclizing the intermediate:

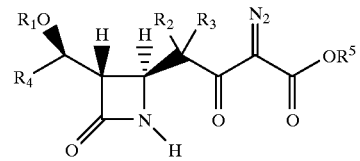

in the presence of rhodium (II) acetate to form a bicyclic ketoester of the formula:

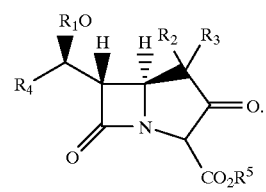

3. A method of preparing intermediates for carbapenem antibiotics comprising the step of treating a N-deprotected acetoxy compound of the formula:

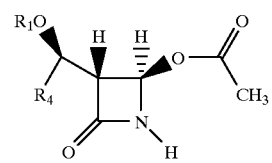

wherein R$_1$ is H, trialkylsilyl, triarylsilyl, diarylalkylsilyl or aryldialkylsilyl, with the alkyl groups having 1–4 carbon atoms and the aryl groups being phenyl or substituted phenyl or p-nitrobenzylcarbonate and R$_4$ is alkyl of 1–4 carbon atoms alkenyl of 2–4 carbon atoms, phenyl, phenyl substituted by 1–3 alkyl groups of 1–3 carbon atoms, 1–3 halogen atoms, 1–3 trifluoromethyl groups, amino, cyano or nitro, with silyl enolether of the formula:

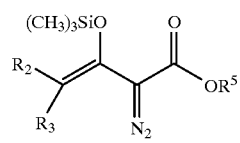

wherein R$_2$ and R$_3$ are H or alkyl of 1–4 carbon atoms, alkenyl of 2–4 carbon atoms, benzyl or phenethyl and R$_5$ is benzyl, allyl, alkyl of 1–4 carbons or p-nitrobenzyl, in the presence of a Lewis acid selected from the group consisting of zinc halide, boron trifluoride etherate, titanium tetrachloride, stannic chloride, and aluminum chloride or silylating agent having sufficient reactivity to yield said intermediate.

4. A method according to claim 3 wherein said step of treating is preceded by a step of deprotecting an acetoxy compound of the formula:

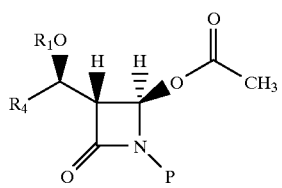
wherein P is a readily removable nitrogen protecting group to produce a N-deprotected acetoxy compound.
* * * * *